US007460910B2

(12) United States Patent
Webb

(10) Patent No.: US 7,460,910 B2
(45) Date of Patent: Dec. 2, 2008

(54) COMMAND SEQUENCING AND INTERLOCKS FOR A REMOTELY PROGRAMMABLE IMPLANTABLE DEVICE

(75) Inventor: James David Webb, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 341 days.

(21) Appl. No.: 11/187,352

(22) Filed: Jul. 20, 2005

(65) Prior Publication Data
US 2006/0074465 A1 Apr. 6, 2006

Related U.S. Application Data

(60) Provisional application No. 60/590,023, filed on Jul. 20, 2004.

(51) Int. Cl.
*A61N 1/00* (2006.01)
(52) U.S. Cl. ....................................... 607/30
(58) Field of Classification Search ................ 607/30, 607/31; 705/3
See application file for complete search history.

(56) References Cited

U.S. PATENT DOCUMENTS 6,480,745 B2 * 11/2002 Nelson et al. ................ 607/60
6,600,952 B1 * 7/2003 Snell et al. ................... 607/31
2001/0031997 A1 * 10/2001 Lee ............................. 607/59
2001/0051787 A1 12/2001 Haller et al.
2002/0123673 A1 9/2002 Webb et al.
2002/0143372 A1 10/2002 Snell et al.
2003/0120324 A1 6/2003 Osborn et al.

FOREIGN PATENT DOCUMENTS

WO WO 01/47410 A2 7/2001
WO WO 03/066159 A2 8/2003

* cited by examiner

*Primary Examiner*—Carl H Layno
*Assistant Examiner*—Brian T Gedeon
(74) *Attorney, Agent, or Firm*—Ingrassia Fisher & Lorenz, P.C.

(57) ABSTRACT

A care provider is able to remotely program a pacemaker, drug pump, neurostimulation device or other an implantable medical device (IMD) by operating a browser application communicating with a server. Following successful authentication to the server, the care provider's browser receives information about one or more operating parameters of the IMD from the server. The care provider provides an instruction from the browser application to the server to modify one or more operating parameters. The server formats a digital program request from the instruction that includes a digital signature or other identification code uniquely identifying the server. The digital program request is then forwarded to the IMD via a remote monitor (IRM) for subsequent verification of the digital identification code and wireless transmission the verified digital program request from the IRM to the IMD.

10 Claims, 4 Drawing Sheets

COMMAND SEQUENCING AND INTERLOCKS FOR A REMOTELY PROGRAMMABLE IMPLANTABLE DEVICE

PRIORITY CLAIM

This application claims priority of U.S. Provisional Patent Application Ser. No. 60/590,023, which was filed on Jul. 20, 2004 and which is incorporated herein by reference.

TECHNICAL FIELD

The present invention is directed generally to components, systems and methods for remotely programming implantable medical devices (IMD) such as pacemakers, neuro-stimulation devices, drug pumps and/or the like.

BACKGROUND

Pacemakers, neuro-stimulation devices, drug pumps and other implantable medical devices (IMDs) are becoming increasingly common, particularly as the population ages. As the name implies, these devices are surgically or otherwise implanted within a patient to provide monitoring and/or therapy for cardiac, neurological and/or other conditions. A conventional pacemaker, for example, is a battery-powered device that applies electrical impulses to a patient's heart to stimulate contractions or "beats". Neurostimulation devices similarly apply electrical impulses to various regions of the spinal cord or other neurologically sensitive regions to alleviate pain or to produce other beneficial effects in the patient. Other IMD therapies include intrathecal drug delivery provided by so-called "drug pumps" that deliver medication (morphine or baclofen, for example) through a catheter directly to an appropriate area, such as the area around the spinal cord. Because the medication is delivered directly to the appropriate region of the patient's body, the patient's symptoms can typically be controlled with a much smaller dose than would otherwise be prescribed with oral medication. Other types of implantable devices include defibrillators, various types of monitors, and the like.

As medical and computing technologies have progressed, IMDs have become capable of applying increasingly sophisticated and elaborate therapies, and of obtaining increasingly detailed information about the patient. IMD therapies can often be uniquely tailored to the particular needs of the patient, provided that adequate information is available while the device is being programmed. If the patient is present within a hospital or a physician's office, for example, adjusting the patient's therapy is a relatively straightforward process of adjusting device parameters (e.g. pacing parameters, drug dosage, etc.) in the IMD with a conventional device programmer. If the patient is not physically present at a treating facility with a suitable device programmer, however, adjustments to IMD programming can be a significant inconvenience. Some patients may need to travel significant distances, for example, and/or may need to appear at the treating facility on a frequent basis until proper parameters are programmed in the device. These trips to the treating facility are inconvenient to both the patient and to the caregiver. Although various systems exist for providing some remote programming functionality (see, for example, commonly assigned United States Patent Publication No. 2002/0123673, which is incorporated herein by reference), it is nevertheless desirable to improve the flexibility, accessibility, security and functionality of such systems.

It is therefore desirable to create systems and techniques capable of providing convenient programming updates to implanted medical devices without requiring the patient to be physically present at the same location as the caregiver that is programming the device. Moreover, it is desirable to create a technique for improving information provided to caregivers without significant effort by the patient. Furthermore, other desirable features and characteristics will become apparent from the subsequent detailed description and the appended claims, taken in conjunction with the accompanying drawings and this background section.

BRIEF DESCRIPTION

According to various exemplary embodiments, a care provider is able to remotely program a pacemaker, drug pump, neuro-stimulation device or other implantable medical device (IMD) by operating a browser application communicating with a server via a conventional digital network such as the Internet. After successfully authenticating to the server, the care provider's browser receives information about one or more operating parameters of the IMD. The care provider provides an instruction from the browser application to the server to modify one or more operating parameters. The server formats a digital program request from the instruction that includes a digital signature or other identification code uniquely identifying the server. The digital program request is then forwarded to the IMD via a remote monitor (IRM) that subsequently verifies of the digital identification code and wirelessly transmits the verified digital program request to the IMD.

In further exemplary embodiments, a digital program request formatted by a remotely-located server is provided to an implantable medical device (IMD) having an identifier associated therewith. The identifier may be any alphanumeric string, cryptography key, code or other digital information capable of identifying the IMD in any manner. Alternatively, the identifier may simply identify an IRM that is assigned or otherwise logically associated with the IMD in any manner. The identifier is provided to the remotely-located server to acquire the digital program request intended for the IMD. The digital program request is validated using a digital identification code that uniquely identifies the server, and the program request is added to a storage queue associated with the IMD upon successful validation. The contents of the storage queue are subsequently transmitted (e.g. via a wireless transmission) to the IMD. In various further embodiments, the connections between the server and the caregiver's browser and/or between the server and the IRM/IMD are encrypted using virtual private network (VPN), secure sockets layer (SSL) and/or other techniques.

In other embodiments, a remote monitoring device for facilitating communication between a server and an implantable medical device (IMD) having an identifier associated therewith suitably includes a wireless interface configured to communicate with the IMD, a network interface configured to communicate with the server, and a processor appropriately configured to execute a software application. The software application is configured to obtain the identifier from the IMD via the wireless interface, to provide the identifier to the server via the network interface to acquire the digital program request intended for the IMD, to validate a digital identification code uniquely identifying the server contained within the digital program request, to add the validated program request to a storage queue associated with the IMD for subsequent wireless transmission to the IMD via the wireless interface, and to store responses to the server in a notification queue for subsequent transmittal to the server via the network interface.

In still other embodiments, digital storage devices and/or systems incorporate similar concepts. These and other exemplary embodiments are described in additional detail below.

BRIEF DESCRIPTION OF DRAWINGS

Various exemplary embodiments will hereinafter be described in conjunction with the following drawing figures, wherein like numerals denote like elements, and.

DETAILED DESCRIPTION

The following detailed description is exemplary in nature and is not intended to limit the invention or the application and uses of the invention. Furthermore, there is no intention to be bound by any theory presented in the preceding background of the invention or the following detailed description of the drawings.

According to various exemplary embodiments, a physician or other medical caregiver is able to remotely yet securely program a medical device implanted in a patient from the convenience of a standard browser application. After authenticating to a network server, the caregiver receives information about the patient's device, and is able to modify device parameters (such as drug dosage or intervals, pacing parameters, and/or the like) within a conventional browser interface. The server receives the instructions from the caregiver in a secure manner, and formulates a digital program request that includes a digital code uniquely identifying the server. The server may also include an identifier for the IMD and/or a sequentially-generated number within the program request to ensure the integrity and security of the request. The program request is transferred to a remote monitor that wirelessly communicates with the patient's IMD. By leveraging the accessibility and convenience of the server on the digital network, the patient and caregiver are no longer required to be physically present at the same location or available at the same time. To the contrary, the patient need only have access to a remote monitor, which may be provided in the patient's home or office, or at another convenient location. Moreover, the server remains in contact with the IMD (via the remote monitor) on at least an intermittent basis in various embodiments, thereby allowing the caregiver to obtain data about the patient's device without requiring travel or other significant effort by the patient. In addition, various techniques and systems shown herein could be equivalently used in "real time" or near real-time embodiments in which a caregiver uses an online server to program a patient's IMD even though the patient may be physically present at the same location as the caregiver and/or available for immediate receipt of the new IMD programming. Such embodiments allow the caregiver to program the IMD without having a specialized programmer for the particular IMD, and may additionally provide further conveniences such as centralized data monitoring, a familiar interface, immediate access to the latest programming techniques and software, and/or the like.

Figure 1:
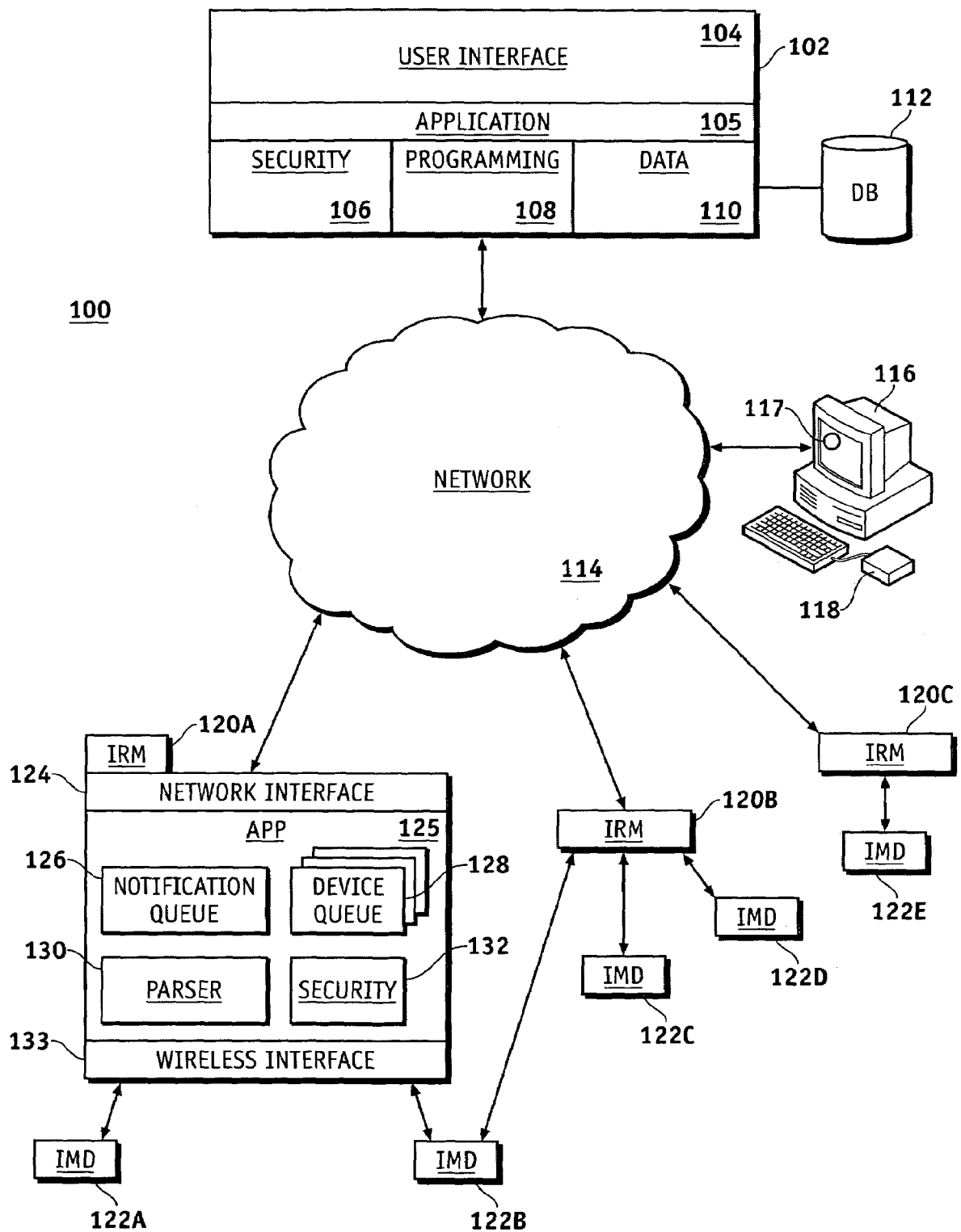
FIG. 1 is a block diagram showing an exemplary system for remotely programming an implantable medical device.

Turning now to the drawing figures and with initial reference to FIG. 1, an exemplary system 100 for remotely programming one or more implantable medical devices 122A-C suitably includes a server 102 communicating with any number of remote monitor devices (IRMs) 120A-C and/or any number of caregiver terminals 116 via network 114. Caregivers suitably interact with server 102 via a browser application 117 executing on terminal 116. After authenticating with server 102, caregivers are able to receive information regarding one or more devices 122A-E, and are able to provide instructions for modifying the programming of devices 122A-E using browser 117. Server 102 appropriately verifies that the instructions provided are safe and consistent with prior instructions, and then formulates a digital program request message that can be transmitted to one or more remote monitors 120A-C for eventual delivery to devices 122A-E. Similarly, information from devices 122A-E may be manually or automatically collected by remote modules 120A-C and forwarded to server 102 for subsequent retrieval by the caregiver, if appropriate.

Network 114 is any communications medium or media capable of providing digital communications between server 102, browser 117 and/or remote monitors 120A-C. In various embodiments, network 114 incorporates the public Internet, although network 114 may equivalently represent any public or private network, including any local area or other network operating within a medical facility. Although FIG. 1 shows network 114 as a single conceptual "cloud", in practice server 102 need not communicate with both browser 117 and remote modules 120A-C via the same physical network. Remote monitors 120A-C and/or terminal 116 may physically connect to network 114 via any type of voice and/or data connections, for example, and network 114 may incorporate any number of dial-up, broadband, fiber optic, wireless, satellite and/or other data links in a wide array of alternate embodiments.

The physician, nurse or other caregiver accesses server 102 via any terminal 116 having access to server 102 via network 114. Terminal 116 is any personal computer, portable computing device, workstation, kiosk, personal digital assistant, wireless telephone or other computing device capable of interacting with server 102 via a browser application 117. Browser 117 is any type of conventional browser such as the Internet Explorer browser application available from Microsoft Corporation of Redmond, Wash., any of the various MOZILLA-based browsers readily available on the Internet, or the like. In various embodiments, terminal 116 includes an optional input device 118 for receiving biometric or other security-related information from the caregiver, although biometric information need not be present in every embodiment.

Server 102 is any host accessible via network 114 that is capable of securely receiving and processing programming instructions for IMDs 122A-E. In various embodiments, server 102 is physically implemented in a data center environment, with one or more server computers configured with appropriate routing, backup, environmental control and other support resources, as well as suitable physical access control to prevent unauthorized persons from gaining access to sensitive data. Although server 102 could be alternatively implemented with a single computing host, block 102 in FIG. 1 is intended as a logical representation that shows functions and features that may be carried out by any number of actual computers.

Server 102 suitably includes a server application 105 that interoperates with any number of modules 106, 108, 110 for such tasks as processing security data, verifying device information, managing data in database 112, and/or other tasks as appropriate. Application 105 may be written in any programming or scripting language, such as the .NET framework available from Microsoft Corp, the JAVA framework available from Sun Microsystems, or the like. Application 105 and modules 106, 108, 110 need not be implemented with separate applications, but may rather incorporate any libraries, object classes, data structures, programming routines or other components capable of providing the described functions. Data management module 110, for example, may be any type of database management program capable of accessing and managing data stored within database 112. Application 105 and modules 106, 108, 110 may be stored in source and/or object code form on any disk drive, memory or other digital storage medium associated with one or more computing hosts within server 102. Particular features of application 105 and its associated modules are described more fully below.

Server 102 also provides a suitable user interface 104 to browser 117, such as any hypertext markup language (HTML), extensible markup language (XML), cascading style sheet (CSS), active server pages (ASP) and/or the like. The appearance of the particular interfaces 104 provided by server 102 vary widely from embodiment to embodiment, but typically incorporate conventional web constructs and structures to provide information and to receive inputs from the user in a convenient format that is readily accessible from a variety of terminals 116.

Server 102 is capable of communicating with any number of remote monitors 122A-C. Although remote monitors 122A-C are commonly referred to as "in-home remote monitors" or simply "IRMs", it is not necessary that the IRMs be actually located in a home. To the contrary, IRMs may be located in homes, offices, nursing homes, hospitals, places of business, retail stores, restaurants, airports, bus terminals, libraries, clinics and/or any other locations for public and/or private use. Using various techniques described herein, each IRM 120A-C may be able to provide inter-communication between server 102 and any number of implanted devices 122A-E. Conversely, patients may be able to update their IMDs 122A-E using any IRM 120A-C operating within system 100 that is recognized by server 102, subject to access control rules, permissions, and the like.

IRMs 120A-C may be implemented with any personal computers, personal digital assistants or other computing devices. FIG. 1 shows IRM 120A with additional detail not reproduced for IRMs 120B-C, but similar modules and features discussed with regard to IRM 120A would typically be present within other IRMs 120B-C as well. In various embodiments, IRMs 120A-C each contain a network interface 124 to network 114, a wireless interface 133 to one or more IMDs 122A-E and a software application 125 stored in any disk drive, memory or other digital storage medium associated with the IRM. Application 125 suitably includes any number of modules 130, 132 capable of parsing data messages received from server 102 and/or of verifying security constructs incorporated within received program requests. Data parsing module 130, for example, may be a module specially intended to parse messages in a particular format (e.g. XML or SOAP) used to exchange information between IRMs 120A-C and server 102. Similarly, security module 130 may be a library or other construct used in decrypting digital signatures contained within program requests, or the like. In various embodiments, application 125 also incorporates two or more logical queues 126, 128 for storing notifications provided to server 102 and program requests provided to an IRM 122A-E, as described more fully below. Each queue 126, 128 may be implemented with any type of stack, tree, array, list or other conventional data structure. In various embodiments, IRM 120 interoperates with multiple IMDs 122A-E, and therefore maintains a separate device queue 128 for each of these devices. Alternatively, each IRM 120 may be associated with only one IMD 128 at a time, thereby allowing a single device queue 128 to suffice in many embodiments.

Figure 2:
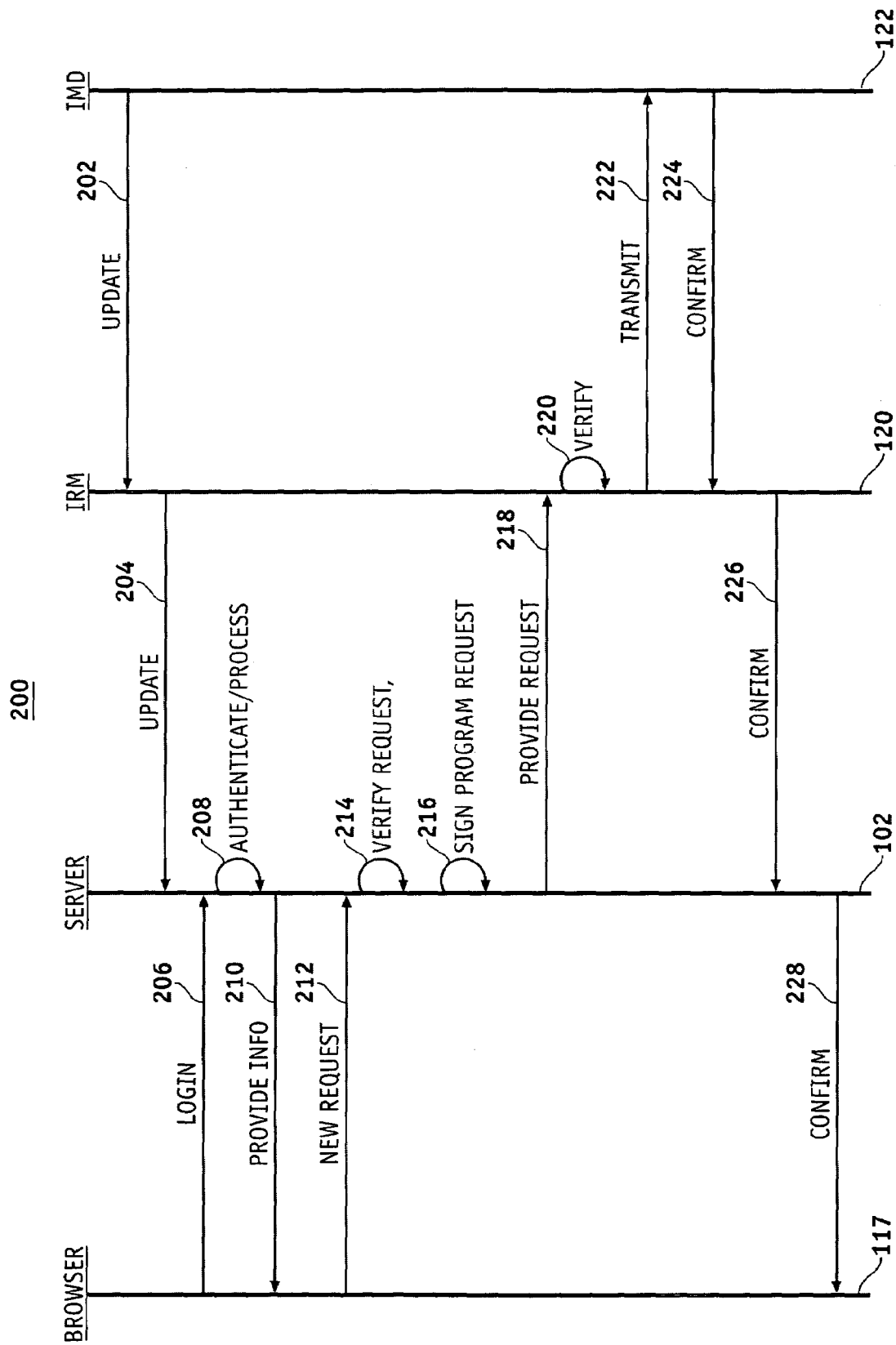
FIG. 2 is a simplified data-flow diagram showing exemplary interactions between a browser, a server, a monitor and a medical device.

System 100 allows caregivers to securely receive information about a patient's IMD 122, to modify one or more parameters of device 122, and to safely provide the caregiver's instructions to IMD 122 via IRM 120. With reference now to FIG. 2, an exemplary process 200 for providing programming instructions from a caregiver's browser 117 to an IMD 122 suitably includes the broad steps of providing IMD data to server 102 (steps 202, 204), establishing a secure connection with browser 117 (steps 206, 208, 212, 214), processing the instructions at server 102 to create a program request (steps 214, 216) that can be provided to IRM 122 (steps 218, 220, 220), and providing results back to server 102 and/or browser 117 (steps 224, 226, 228). The particular process shown in FIG. 2 is intended as exemplary only. In practice, the various steps shown in the figure may be executed in any temporal order, and/or various steps may be combined, supplemented or eliminated as appropriate.

IMDs 122 are associated with one or more IRMs 120 in any manner. In various embodiments, a caregiver or other administrator assigns the IMD 122 to one or more eligible IRMs 120 by creating an association in database 112 that is verified on server 102 before program requests are provided (e.g. in step 214). Alternatively, a patient is able to associate his or her IMD 122 with any available IRM 120 by simply using the IRM 120 to perform a status update (step 202). The patient simply places the IRM 120 within wireless range of device 122, and then manually or automatically activates the IRM. IRM 120 suitably communicates with IMD 120 via an infrared, radio frequency or other wireless link to obtain identifying information about IMD 120. Such information may include any identifer that uniquely identifies the particular IMD 122 present at IRM 120. Examples of identifiers available from different types of IMDs 122 include serial numbers, alphanumeric strings, cryptography keys, digital codes and/ or the like. For devices that do not include such numbers (or that have serial numbers that are easily modified or reset), a conventional handshaking technique can be used to identify the particular IMD 120. Other embodiments could equivalently identify IMD 122 using an identifier code from an IRM 122 that is associated with a particular IMD in database 112 or elsewhere within server 102.

IRM 120 also obtains status information about IMD 122 (e.g. battery power, type of drug present, drug concentration, a sequential number associated with a last program request, and/or any other information). This status information, along with the identifying information about IMD 122, can be transmitted to server 102 across any medium (step 204). Data transferred between server 102 and IRM 120 may be formatted in any manner, using any standard or non-standard data formatting conventions. Messages may be formatted in XML and/or SOAP format, for example. In various embodiments, IRM 120 and server 102 communicate across a secure connection such as a virtual private network (VPN), secure sockets layer (SSL) connection, or the like to prevent unauthorized parties from intercepting or observing data packets sent between IMD 1220 and server 102. Again, IRM 120 may associate itself with one or more IMDs 122 in any manner, and may share this association with server 102 as appropriate. Server 102 suitably stores status information in database 112 for subsequent retrieval.

As noted above, caregivers or other authorized persons communicate with server 102 via a conventional browser program 107 (step 206). In an exemplary interaction, browser 107 establishes a secure data connection with server 102 using VPL/SSL techniques or the like, and requests access to system 100 (step 206). As part of the access request, browser 107 suitably provides a digital credential to verify that the caregiver using browser 107 is authorized to gain access to system 100. The digital credential may be a simple userid/password pair, or may involve stronger authentication such as a digital signature, a biometric identifier (e.g. a voice or finger print, retinal scan, etc.), or an identifier obtained from a digital token (e.g. a physical device in the possession of an approved user that provides a digital code or other information that can be used to authenticate the user). Server 102 processes the access request to authenticate the caregiver (step 208), and grants appropriate access to the caregiver if authentication is successful. Access provided to each authorized user of system 102 may be administered in any manner. In an exemplary embodiment, a rules-based access system is based upon access privileges stored in database 112 for each user. Privileges may be assigned by patient, by IMD 122, by IRM 120, and/or in any other appropriate manner. In various embodiments, browser 117 also authenticates server 102 using cryptographic techniques or the like to ensure that data provided by server 102 is legitimate. Authentication may involve the use of a public key associated with server 102, for example, which can be verified using conventional virtual private network (VPN) techniques, secure sockets layer (SSL) encryption, or the like.

Upon successfully authenticating with server 102, the caregiver gains access to authorized information in database 112 (step 210). This information may be retrieved (e.g. through any set of queries posited by data module 110 to database 112 in response to requests generated by browser 107) and presented to the caregiver in any manner. Caregivers may request a list of authorized patients, for example, or may request information associated with a particular patient or device, or may view recent program requests for all patients, or the like. When possible, server 102 provides current operating parameter information (e.g. current drug, current dosage, current drug concentration, pacing parameters, etc.) to browser 107 to assist the caregiver in evaluating the patient. Additionally, various embodiments of server 102 may provide more advanced information based upon data obtained from the IMD 122 and/or computed in conduction with IRM 120, as described more fully below. Such information may contain indications of unusual behaviors observed by the device, for example, or may include computed values such as daily maximal doses computed based upon drug concentrations present in the device, estimated time to reservoir empty, and/or other parameters as appropriate.

If the caregiver wishes to issue instructions for a change in one or more device parameters, such instructions are provided from browser 107 to server 102 (step 212). The received instructions may be verified or otherwise evaluated at server 102 (e.g. by module 108) to ensure that the instructions are consistent with the current status of IMD 122 and/or that no safety parameters (e.g. recommended dosages, etc.) maintained in database 112 are exceeded.

After verifying the new programming instructions received from the caregiver, server 102 suitably formats a digital program request that can be provided to the IRM 120 associated with the IMD 122 of interest. The program request may be formatted in any manner (e.g. simple object access protocol (SOAP), conventional XML and/or the like) that can be interpreted by IRM 120. Additionally, server 102 digitally signs or otherwise places a unique digital identifier in the program request to prevent rogue parties from emulating server 102 (step 216). Additionally, server 102 may provide a sequential or other unique transaction identifier number in the program request to prevent IMD 122 from processing programming requests out of order, and to prevent replay attacks wherein legitimate data packets are duplicated and re-transmitted to the recipient after the intended time. The resulting digitally-signed (or otherwise protected) program request is then stored in a queue for subsequent transmittal to the IRM 120 associated with the particular IMD 122.

Transfer of the program request to IRM 120 is handled in any manner (step 218). In various embodiments, each IRM 120 polls server 102 at a regular or irregular interval to receive any updates queued since the last poll. Alternatively, server 102 generates a notification message to IRM 120 and/or to the patient (e.g. an email) that a new program request is waiting on the server. In still other embodiments, updates remain queued until IRM 120 attempts to connect to server 102 for any purpose. As mentioned above, the connection between server 102 and IRM 120 may be any secure or unsecure connection (e.g. VPN/RSS) as appropriate. IRM 120 suitably verifies the digital information code contained within each program request prior to actually programming IMD 122 to further ensure that the program request is legitimate and from a trusted source (step 220). This digital credential may be a digital signature generated with a private key associated with server 102, for example, that allows IMD 122 to de-crypt the signature using server 102's public key, thereby verifying the authenticity of the message. In various embodiments, server 102 also authenticates IRM 120 before transferring the program requests to ensure that IRM 120 is a legitimate data recipient. Such authentication may involve using digital signatures, private codes or other identification information about IRM 120 as appropriate. The verified program request is then applied to IMD 122 (step 222), and any status reports may be provided from IMD 122 to IRM 120, server 102 and/or browser 107. IRM 120 and IRM 122 may additionally authenticate to each other using private codes, digital signatures or other techniques to further enhance the security of process 200, although this is not required in all embodiments.

Figure 3:
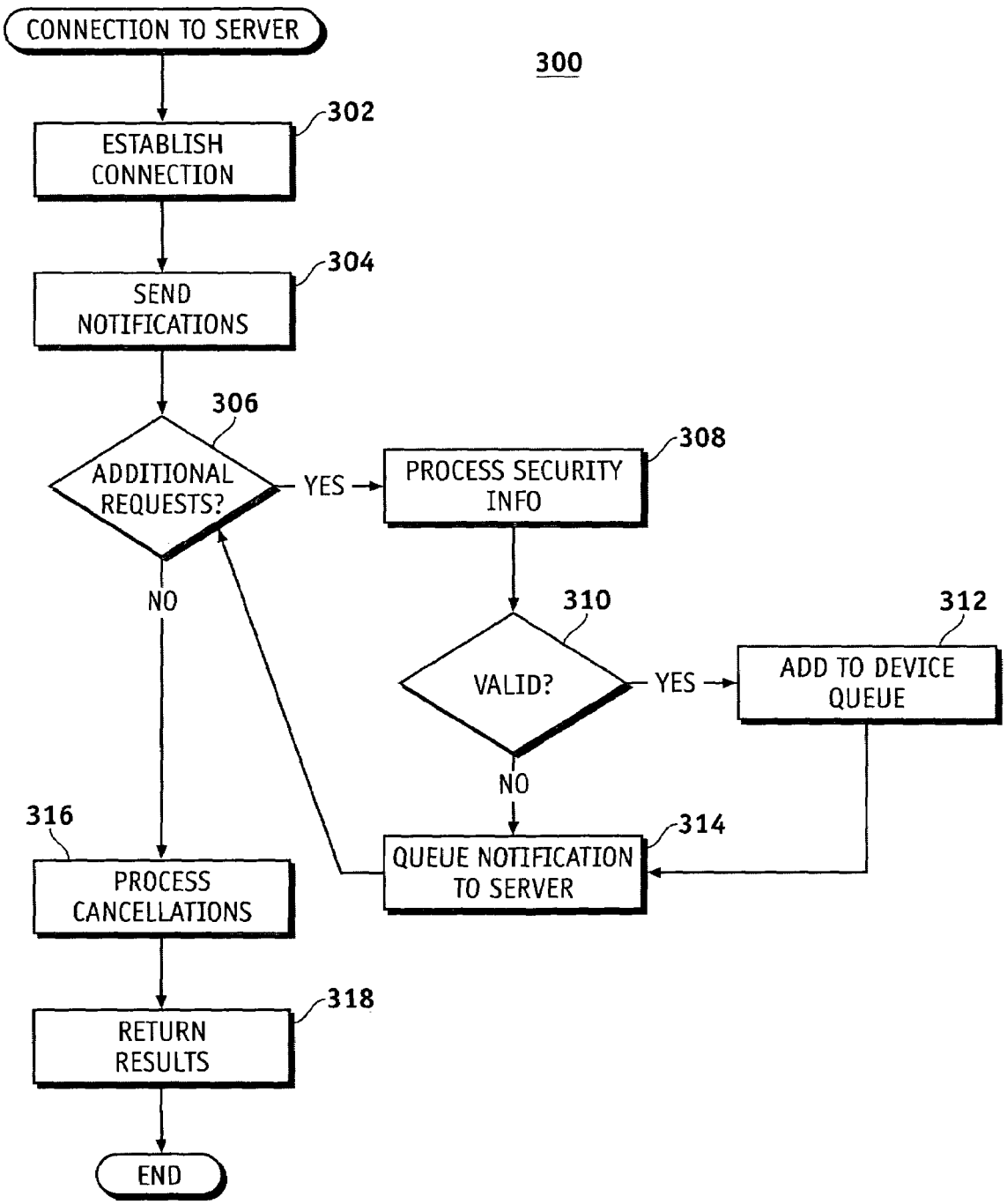
FIG. 3 is a flowchart of an exemplary process for transferring programming requests from a server to a remote monitor.
Figure 4:
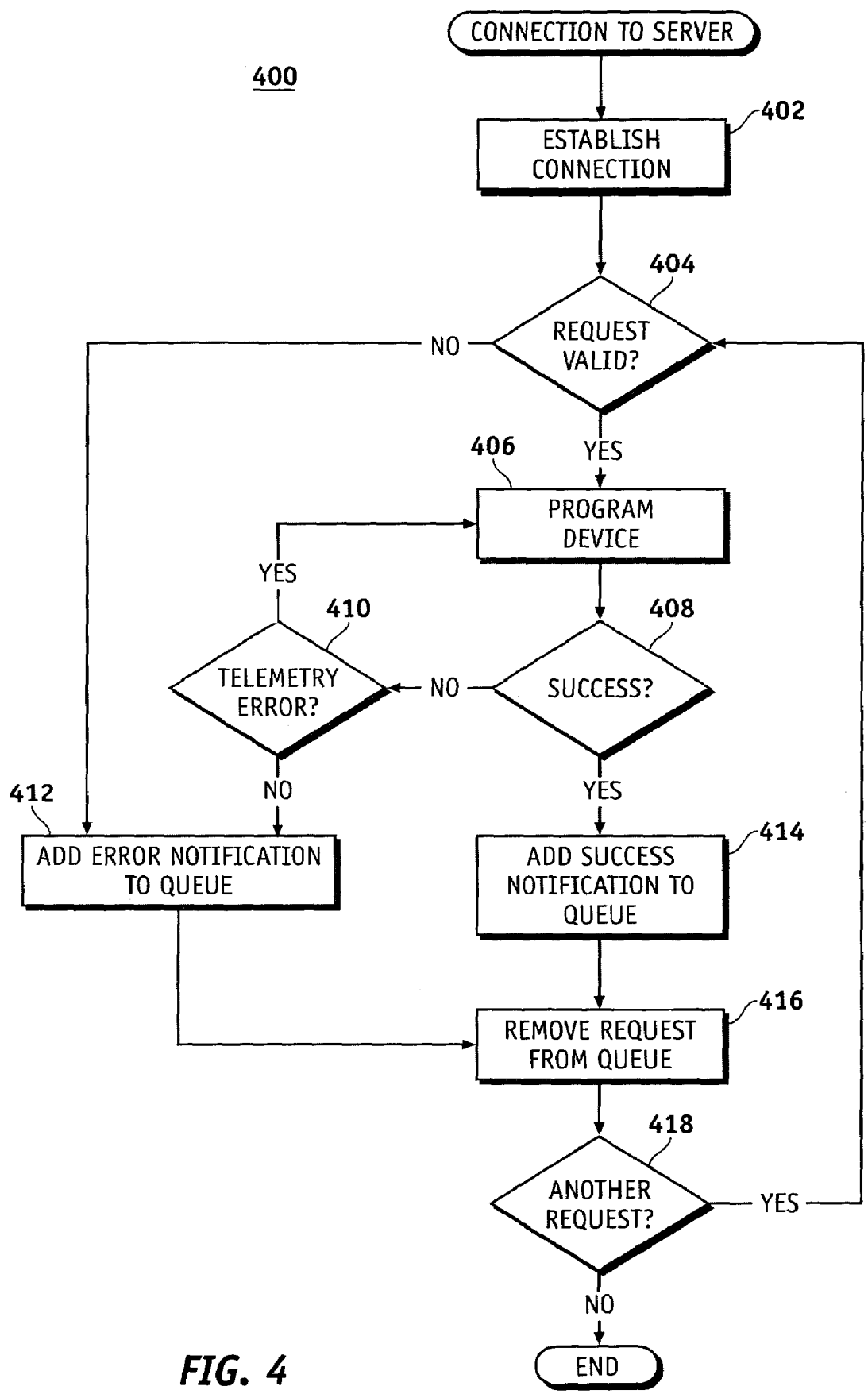
FIG. 4 is a flowchart of an exemplary process for transferring programming requests from a remote monitor to a medical device.

By using various cryptographic and other security techniques, the reliability of program requests and other data can be maintained even in environments that incorporate public networks. To reiterate, various embodiments authenticate the caregiver to server 102 using passwords, tokens, biometrics, digital signatures or other techniques to ensure that the caregiver is truly authorized to obtain data and/or issue program requests. The caregiver's browser may optionally authenticate server 102 using VPN/SSL or other techniques to ensure that received information is reliable and not visible to other parties on network 114. IRM 122 ensures that data received from server 102 is signed or otherwise protected with digital signatures or other techniques before the program is applied to IMD 122, and may also receive sensitive data over secure links (e.g. connections protected with VPN, SSL or other security). Further, various embodoiments allow server 102, IRM 120 and/or IMD 122 to additionally authenticate to each other using any type of signatures, codes or the like to further enhance the level of security and reliability within system 200. Additional security, data integrity and/or other data checks may also be contained within various embodiments. Further detail about exemplary data exchange processes 300, 400 executed within various embodiments of IRM 120 are shown in FIGS. 3 and 4. Each of these processes may be implemented with any type of computer-executable instructions stored in any digital storage medium (e.g. disk drive, flash or other memory) and executed by any processor residing within IRM 120.

With reference now to FIG. 3, an exemplary process 300 for retrieving program requests from server 102 to IRM 120 suitably includes the broad steps of establishing a connection to server 102 (step 302), sending any queued notifications to server 102 (step 304), verifying the digital security information contained within the program request (steps 308, 310), placing messages into the appropriate queues for subsequent action (steps 312, 314) and processing any cancellation messages (step 316).

As noted above, the connection to the server 102 (step 302) may be established in response to a patient instruction, an interaction with IMD 122), or may be established at regular or irregular intervals. In various embodiments, the patient or other user places IRM 120 in a cradle and depresses a button to establish a telephone, wired or wireless connection to network 104, which in turn provides access to server 102. If notification queue 126 (FIG. 1) has notifications, these are generally delivered at the outset of the connection (although alternate embodiments could deliver notifications at the end of the connection, in a separate connection, and/or at any other point in time). These notifications include responses to status requests received from server 102, as well as any patient-initiated status updates.

In various embodiments, IRM 120 provides the digital identification number (e.g. serial number) of the associated IMD 122 to server 102 to request any messages intended for the IMD 122 indicated by the digital identification number. In equivalent embodiments, server 102 is aware of the relationship between IRM 120 and IMD 122 prior to the connection. In either case, any program requests and other messages intended for one or more IMDs 122 associated with IRM 120 are transferred to IRM 120 over network 114 in any suitable format (e.g. XML, SOAP, etc.). Each of the requests provided (step 306) are processed in turn following receipt by IRM 120. Processing (step 308) suitably involves verifying that the digital signature or other security information contained within the program request uniquely identifies server 102 as the originator of the message. Processing 308 may also include checking a serial number or other IMD identifier contained within the message against the identifier information maintained by IRM 120, and may also include checking the sequential number to ensure that the program request is not being processed out of order, and is only delivered to IMD 122 once. IRM 120 may also compare an optional time of creation value contained in the message to a current time and/or a time of receipt to further improve the reliability of the message. In such embodiments, IRM 120 may periodically or aperiodically synchronize its system clock with server 102 using, for example, the network time protocol (NTP) or the like.

Upon successful validation, the validated program request is added to device queue 128 for subsequent programming in IMD 122. IRM 120 may also provide an indication (e.g. a visual or audio signal) to notify the patient that the IRM 120 should be synchronized with the patient's IMD 122. If ERM 120 is unable to validate the message, a notification is placed in notification queue 126 to alert server 102 at the next opportunity.

After all of the received requests are processed (step 306), any cancellations are processed (step 316) by IRM 120. Occasionally, a caregiver may wish to cancel a previously-sent program request, so IRM 120 suitably processes such requests after the message requests are received. A cancellation request may indicate a particular program request (e.g. by sequential number) that should be removed from device queue 128, or may indicate that all program requests having sequential numbers that precede the sequential number in the cancellation request should be removed from device queue 128 and discarded.

After processing the various program requests and other messages, IRM 120 optionally provides a status update to server 102 (step 318), and terminates the connection as appropriate. The status update may include a simple count of the number of message correctly received, and/or may include identifiers of each message. This information is provided to server 102 for storage within database 114 and/or updating of a display on the caregiver's browser 107.

In various optional embodiments, IRM 120 contains a visual display and/or audio speaker for providing information directly to the patient. In such embodiments, the patient may be notified (e.g. by a audio signal, flashing light or the like) that new programming is available for IMD 122. IRM 120 may further display information about IMD 122, status information about the transfer process, lists of programs received (which may be sorted in any manner, e.g. by time of creation, sequential number, or any other value), and/or any other information as appropriate. Other embodiments of IRM 120 contain only limited feedback capabilities (e.g. simple lights or audio signals) or provide no feedback to the user, as appropriate.

With final reference now to FIG. 4, an exemplary process 400 for connecting to an IMD 122 from IRM 120 suitably includes the broad steps of establishing a wireless connection (step 402), verifying that the transferred messages are valid (step 404), programming the device with the validated request (step 406), determining the result of the programming (steps 408, 410) and placing proper status messages in the notification queue 126. As noted above, the connection 402 between IRM 120 and IMD 122 is typically a wireless connection such as an infrared, radio frequency or similar connection. The connection may be initiated by placing IRM 120 in proper location with respect to IMD 122 to allow communication, by activating a button on IRM 120, and/or by any other technique.

For each request in the device queue (step 418), IRM 120 again verifies that the request is valid and properly signed by server 102, and optionally double-checks the IMD identification and/or sequential code contained in the program request. This verification ensures that the request was not tampered with, contaminated or otherwise modified while stored in device queue 128. Alternatively or additionally, step 418 is partially or entirely performed within IMD 122. Although such functionality may increase the data processing demands on IMD 122, end-to-end cryptography from server 102 to device 122 would further enhance the security and reliability of data contained within the program request.

In many conventional embodiments, IRM 120 programs IMD 122 using information contained within the program requests as appropriate (step 406). Programming in most cases involves simply transferring the program update to IMD 122, but may alternately involve additional processing, error checking, confirmation, etc. by IRM 120 and/or IMD 122 as well. In various embodiments, IRM 120 and/or IMD 122 verifies that information contained within the program request is consistent with the present state of IMD 122 before adjusting the operating parameters of IMD 122. For example, the type and/or concentration of a drug present within a drug pump could be verified to ensure that the dosage prescribed within a program request is consistent with the current state of the device, and/or with any other applicable parameters (e.g. maximum or minimum dosage limits, temporal dosage constraints, and/or the like). A single programming request may therefore result in multiple downlinks to IMD 122, as transactional information (e.g. drug type or concentration) is passed between IMD 122 and IRM 120 and/or server 102.

In still further embodiments, IRM 120 and/or IMD 122 may make further calculations based upon information that may not have been available to the caregiver via server 102. Such calculations may determine a proper value of an operating parameter for IMD 122 based at least in part upon information contained in the program request, as well as information received from the IMD. If a drug concentration presently held by a particular IMD 122 is not known to server 102, for example, various embodiments of server 102 would allow the caregiver to write the prescription in terms of mass (e.g. milligrams) or other information then available. IRM 120 and/or IMD 122 would then determine and program the proper dosage volume using the drug concentration information (e.g. the number of milligrams of drug per milliliter of fluid) contained within the device. If a physician wanted to prescribe two grams of morphine, for example, but did not know the exact concentration of morphine contained within the patient's implanted drug pump, the physician could simply prescribe the two grams using browser 117 and server 102, with IRM 120 and/or IMD 122 determining the exact dosage volume based upon the concentration contained in the device (e.g. if the concentration is 2 g/ml, the device would be programmed to deliver a 1 ml dose). Similar concepts could be applied to any type of information or operating parameters relating to any type of IMD 122. This functionality is optional, however, and may be modified, supplemented or eliminated in other embodiments.

If programming is successful (step 408), a "success" message is placed in notification queue 126 for subsequent forwarding to server 102 (step 414). Similarly, a non-successful result may result in a corresponding message being placed in notification queue 126 (step 412) to indicate the occurrence and/or type of error observed. If the error is a simple telemetry error between the IRM 120 and IMD 122 (step 410), IRM 120 may simply try programming IMD 122 again until a set number of attempts are made, until a timeout occurs, or until further attempts are interrupted for some other reason. The contents of notification queue 126 indicating success or errors in the programming process are appropriately provided to server 102 upon the next initiation of contact with the server (e.g. process 300).

With general reference again to FIG. 1, various systems and techniques for securely and reliably programming an implantable device 122A-E from a conventional browser application 117 have been described. A caregiver suitably authenticates and/or establishes a secure connection with a server 102 using browser 117. Server 102 authenticates the caregiver, and optionally provides information obtained from one or more IMDs 122A-E such as drug type, drug concentration, dosing history, any previously-entered notes, and/or the like. Alternatively, if current information (e.g. drug concentration) is not available, the physician is able in some embodiments to request a new program the device based upon available information, with IRM 120 and/or device 122 applying missing information as needed. If the caregiver does request additional programming that would modify one or more operating parameters of device 122A-E, server 102 suitably formats a digital program request that contains a digital signature or other credential uniquely identifying the server, and that optionally includes additional verification information such as a sequential number, a serial number or other identifier for the recipient IMD 122, and/or the like. The information is provided to a remote monitor 120, which may also be authenticated and/or contacted via a secure channel for ultimate transmission to IMD 122. By applying cryptographic and other secure interlocks between browser 107, server 102, IRM 122 and/or IMD 122, the security and reliability of program requests can be ensured through even inherently unsecure and/or unreliable media such as the Internet. Because caregivers are able modify device parameters from a conventional browser, caregivers and patients are no longer required to be present in the same physical location and at the same time with a device programmer.

Accordingly, various methods and systems for programming a remote IMD from a conventional browser application are provided. While exemplary embodiments have been presented in the foregoing detailed description of the invention, it should be appreciated that a vast number of equivalent variations exist. While much of the system is described as operating in a "store and forward" manner, for example, similar concepts could be equivalently applied in real-time (or near real-time) to allow a caregiver to program an IMD 122 using a conventional web browser 117. As a result, the "remote" IRM 120 and/or IMD 122 need not be physically remote from the caregiver in all embodiments, but could actually be present within the same hospital, clinic, office or other environment. Similarly, server 102 may be implemented on a wide-area basis (e.g. provided by an IMD manufacturer or other provider for intended use by multiple caregivers), and/or may be implemented on a more localized basis, with a particular server 102 supporting those IMDs associated with a hospital, clinic, medical practice, geographic area or the like. Indeed, browser 117 and server 102 could equivalently exist within a single personal computer, network or other host environment, which may be particularly useful for testing, smaller-scale implementations, and other uses.

It should also be appreciated that these exemplary embodiments are only examples, and are not intended to limit the scope, applicability, or configuration of the invention in any way. Rather, the foregoing detailed description will provide a convenient road map for implementing an exemplary embodiment of the invention. Various changes may be made in the function and arrangement of elements described in an exemplary embodiment without departing from the scope of the invention as set forth in the appended claims and their legal equivalents.

What is claimed is:

1. A method for allowing a care provider operating a browser application communicating with a server to modify an operating parameter of a medical device (IMD) implanted in a patient, the IMD communicating with the server via a monitor (IRM), the server storing safety parameter data related to the IMD, the method comprising the steps of:

processing an access request received from the browser application at the server to authenticate the care provider;

if authentication of the care provider is successful, providing information about the operating parameter from the server to the browser application;

receiving an instruction at the server from the browser application to modify the operating parameter;

formatting a digital program request from the instruction at the server, the program request comprising a digital identification code uniquely identifying the server;

forwarding the digital program request to the IRM for subsequent verification of the digital identification code and wireless transmission of the verified digital program request to the IMD;

comparing the instruction to the safety parameter data stored on server; and providing a notice to the care provider if the instructions are inconsistent with the stored safety parameter data.

2. The method of claim 1 wherein the formatting step comprises assigning a sequential code to the digital program request, and wherein the IRM is operable to compare the sequential code to a second sequential code earlier received by the IMD to verify that the digital program request is not received out-of-order.

3. The method of claim 1 further comprising the step of queuing the digital program request until a request for connection is received from the IRM.

4. The method of claim 3 further comprising the steps of comparing an IMD identifier contained within the request for connection to a previously-stored identifier for the IMD prior to forwarding the digital program request to the IRM.

5. The method of claim 1 wherein the access request comprises at least one digital credential uniquely associated with the care provider, wherein the digital credential is selected from the group consisting of a digital signature, a biometric identifier, and an identifier provided by a digital token.

6. The method of claim 1 further comprising the step of receiving an update message from the IRM, the update message comprising an indication of the successful delivery of the digital program request.

7. The method of claim 1 wherein the operating parameter comprises at least one of the group consisting of an allowed dose, an allowed dose interval, an allowed activation dose, and an allowed activation dose interval.

8. The method of claim 1 further comprising the step of updating the information about the operating parameter provided to the care provider in response to the instruction.

9. A server system for use in conjunction with a browser application operable by a care provider, a medical device (IMD), and a monitor (IRM) permitting communication between the server system and the IMD, the server system comprising:

a processor; and a digital storage medium, the digital storage medium having computer-executable instructions stored thereon instructing the processor to:

process an access request received from the browser application at the server system to authenticate the care provider;

if authentication of the care provider is successful, provide information about the operating parameter from the server system to the browser application;

receive an instruction at the server system from the browser application to modify the operating parameter;

format a digital program request from the instruction at the server system, the program request comprising a digital identification code uniquely identifying the server system;

forward the digital program request to the IRM for subsequent verification of the digital identification code and wireless transmission of the verified digital program request to the IMD;

compare the instruction to the safety parameter data stored on server system; and provide a notice to the care provider if the instructions are inconsistent with the stored safety parameter data.

10. The method of claim 1 wherein the IRM stores safety parameter data related to the IMD, and wherein the method further comprises the steps of:

comparing the instruction to the safety parameter data stored on the IRM; and canceling the instructions if the instructions are inconsistent with the safety parameter data stored on the IRM.

* * * * *